United States Patent
Gisler

(10) Patent No.: US 12,408,926 B2
(45) Date of Patent: Sep. 9, 2025

(54) SURGICAL SAW BLADE

(71) Applicant: DEPUY SYNTHES PRODUCTS, INC., Raynham, MA (US)

(72) Inventor: Stefan Gisler, Oberdorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 231 days.

(21) Appl. No.: 17/937,243

(22) Filed: Sep. 30, 2022

(65) Prior Publication Data

US 2023/0013089 A1 Jan. 19, 2023

Related U.S. Application Data

(63) Continuation of application No. 16/657,524, filed on Oct. 18, 2019, now Pat. No. 11,490,898.

(51) Int. Cl.
  *A61B 17/14* (2006.01)
  *A61B 17/16* (2006.01)
  *A61B 17/00* (2006.01)

(52) U.S. Cl.
  CPC ........ *A61B 17/142* (2016.11); *A61B 17/1637* (2013.01); *A61B 2017/00477* (2013.01)

(58) Field of Classification Search
  CPC .............................. A61B 17/142; B23D 61/006
  See application file for complete search history.

(56) References Cited

U.S. PATENT DOCUMENTS 5,122,142 A * 6/1992 Pascaloff ............. A61B 17/142
  D24/146
D337,160 S * 7/1993 Evans .......................... D24/146
(Continued)

FOREIGN PATENT DOCUMENTS

DE 202006009423 U1 8/2006
DE 102010014917 A1 10/2011
(Continued)

OTHER PUBLICATIONS

Notice of Refusal issued on Mar. 19, 2024 for JP Patent Appl. No. 2022-522912.

*Primary Examiner* — Zade Coley
(74) *Attorney, Agent, or Firm* — Kramer & Amado, P.C.

(57) ABSTRACT

A surgical saw blade has an upper surface and a lower surface, and includes a first end having right and left side edges, where the first end is configured to connect to an oscillating head of a powered saw. The saw blade also has a cutting end; and an elongated shank connecting the first end and the cutting end. The first end of the saw blade may be narrower than the shank, and a stopping surface may connect the first end to the elongated shank. The stopping surface is configured to engage the oscillating head of the powered saw, so as to ensure correct positioning of the saw blade relative to the oscillating head. The elongated shank of the saw blade may have an elongated hole through the shank, where the size and shape of the elongated hole are configured to optimize a resonant frequency and/or a dynamic stiffness of the saw blade. The cutting end of the saw blade may have a plurality of first teeth thereon, where each first tooth is mounted on a distal end of a tine. Each pair of adjacent tines is separated by a longitudinal slot, with a distal end of each longitudinal slot being bridged by a web connecting a corresponding pair of adjacent tines.

10 Claims, 8 Drawing Sheets

(56) References Cited

U.S. PATENT DOCUMENTS

| | | | |
|---|---|---|---|
| 5,263,972 A * | 11/1993 | Evans | B23D 51/10 |
| | | | 606/176 |
| 6,113,618 A * | 9/2000 | Nic | B23D 61/123 |
| | | | D24/146 |
| D459,805 S | 7/2002 | Pascaloff | |
| 6,656,186 B2 * | 12/2003 | Meckel | A61B 17/142 |
| | | | 606/178 |
| D489,823 S | 5/2004 | Fisher | |
| D492,412 S * | 6/2004 | Desoutter | D24/146 |
| D525,707 S | 7/2006 | Kullmer | |
| 7,704,254 B2 | 4/2010 | Walen | |
| D627,464 S | 11/2010 | Nelson | |
| 8,100,912 B2 * | 1/2012 | Marietta | A61B 17/142 |
| | | | 606/176 |
| 8,216,262 B2 * | 7/2012 | O'Donoghue | A61B 17/142 |
| | | | 606/86 R |
| 8,444,647 B2 | 5/2013 | Walen et al. | |
| 8,696,673 B2 | 4/2014 | Walen et al. | |
| 9,060,783 B2 | 6/2015 | Walen et al. | |
| D742,002 S | 10/2015 | Fisher | |
| 9,192,390 B2 * | 11/2015 | delRio | B23D 59/002 |
| 9,820,753 B2 | 11/2017 | Walen | |
| 10,342,553 B2 | 7/2019 | Gilhooley | |
| D882,789 S | 4/2020 | Qun | |
| D939,697 S | 12/2021 | Servedio | |
| D940,320 S | 1/2022 | Schaz | |
| D989,309 S | 6/2023 | Levy | |
| D996,166 S | 8/2023 | Kazda | |
| 2002/0104421 A1 * | 8/2002 | Wurst | B23D 61/021 |
| | | | 83/835 |
| 2004/0199167 A1 * | 10/2004 | Fletcher | B23D 61/006 |
| | | | 606/82 |
| 2005/0245935 A1 * | 11/2005 | Casey | A61B 17/142 |
| | | | 606/82 |
| 2006/0206100 A1 * | 9/2006 | Eskridge | A61B 17/142 |
| | | | 606/1 |
| 2007/0123893 A1 * | 5/2007 | O'Donoghue | A61B 17/142 |
| | | | 606/82 |
| 2008/0269755 A1 * | 10/2008 | Malackowski | A61B 17/142 |
| | | | 606/82 |
| 2009/0093815 A1 * | 4/2009 | Fletcher | B23D 51/10 |
| | | | 606/82 |
| 2010/0262148 A1 * | 10/2010 | O'Donoghue | A61B 17/142 |
| | | | 606/82 |
| 2010/0292701 A1 * | 11/2010 | Fisher | A61B 17/142 |
| | | | 606/82 |
| 2016/0081697 A1 * | 3/2016 | Carusillo | A61B 17/142 |
| | | | 606/82 |
| 2018/0064447 A1 * | 3/2018 | Koljaka | A61B 17/142 |
| 2019/0231364 A1 | 8/2019 | Walen et al. | |
| 2019/0298404 A1 * | 10/2019 | Stritch | A61B 17/320758 |
| 2020/0138451 A1 * | 5/2020 | Ferro | A61B 17/142 |
| 2023/0190327 A1 | 6/2023 | Lark | |
| 2023/0263534 A1 | 8/2023 | Kowall | |

FOREIGN PATENT DOCUMENTS

| | | | | |
|---|---|---|---|---|
| DE | 102011056927 A1 | 6/2013 | | |
| EP | 274876 A1 | 7/1998 | | |
| EP | 3769701 A2 * | 1/2021 | | A61B 17/142 |
| JP | 2009-511150 A | 3/2009 | | |
| JP | 2009-201059 A | 9/2009 | | |
| WO | WO-2007045993 A2 * | 4/2007 | | A61B 17/14 |

* cited by examiner

SURGICAL SAW BLADE

CROSS-REFERENCE TO RELATED APPLICATIONS

This is a Continuation of application Ser. No. 16/657,524, filed Oct. 18, 2019. The entire disclosure of the prior application is incorporated by reference herein in its entirety.

FIELD

This invention relates generally to surgical saw blades for use with a powered saw.

BACKGROUND

Surgical saws have been widely used for performing bone surgery. Many such saws have employed an elongated saw blade having a toothed segment on one end thereof, with a pivotal mount which permits angular oscillation at the other end. Blades which oscillate in an angular fashion may provide wide cutting motion at the blade tip. In some cases, minimal cutting motion may be desired to minimize trauma to the patient.

SUMMARY OF THE INVENTION

In light of the present need for improved surgical saw blades, a brief summary of various exemplary embodiments is presented. Some simplifications and omissions may be made in the following summary, which is intended to highlight and introduce some aspects of the various exemplary embodiments. Detailed descriptions of exemplary embodiments adequate to allow those of ordinary skill in the art to make and use the concepts disclosed herein will follow in later sections.

Various embodiments disclosed herein relate to a surgical saw blade having an upper surface and a lower surface. The saw blade may include a first end having right and left side edges, the first end being configured to connect to an oscillating head of a powered saw; a second end having a plurality of teeth thereon; and an elongated shank having right and left side edges, where the elongated shank connects the first and second ends. In various embodiments, the first end is narrower than the elongated shank, and a stopping surface connects the first end to the elongated shank. The stopping surface may be configured to engage the oscillating head so as to ensure correct positioning of the saw blade relative to the oscillating head.

In various embodiments, the surgical saw blade has a stopping surface which includes a first stopping surface connecting the right side edge of the first end of the saw blade to the right side edge of the elongated shank; and a second stopping surface connecting the left side edge of the first end to the left side edge of the elongated shank. The first and second stopping surfaces may be configured to engage the oscillating head.

In various embodiments, the first end of the saw blade has an upper surface and a lower surface, with a hole in the first end extending from the upper surface to the lower surface. The upper surface and the lower surface of the first end of the saw blade may be configured to engage first and second clamping surfaces on the powered saw. The hole in the first end may be configured to engage an elevated ridge on at least one of the first and second clamping surfaces.

Various embodiments disclosed herein relate to a surgical saw blade having an upper surface and a lower surface. The saw blade may include a first end having right and left side edges, the first end being configured to connect to an oscillating head of a powered saw; a second end having a plurality of teeth thereon; and an elongated shank having right and left side edges, where the elongated shank connects the first and second ends. In various embodiments, the elongated shank has an upper surface and a lower surface, with at least one hole in the shank extending from the upper surface to the lower surface. In various embodiments, the hole in the shank is configured to optimize the resonant frequency of the saw blade. The hole in the shank may be configured to ensure that a resonant frequency of the saw blade is greater than an oscillation frequency of the oscillating head of the powered saw.

The size and shape of the at least one hole may be selected so as to ensure that the resonant frequency of the saw blade is greater than an oscillation frequency of the saw during a cutting operation, thereby ensuring that the saw blade does not resonate during use. In various embodiments, the hole is an elongated hole, which may be configured to control a resonant frequency of the saw blade. In various embodiments, the hole in the shank may be an elliptical hole, a round hole, or a polygonal hole. The elongated hole may also be selected so as to optimize a dynamic stiffness of the saw blade. In various embodiments, the hole in the shank may be a single large round hole. Some embodiments disclosed herein may include a series of multiple small holes in the shank, instead of a single round or elongated hole.

In various embodiments, the surgical saw blade has an elongated shank with an upper surface and a lower surface, with a plurality of holes in the shank extending from the upper surface to the lower surface. The plurality of holes may be configured to ensure that a resonant frequency of the saw blade is greater than an oscillation frequency of the oscillating head. The plurality of holes in the shank may be a plurality of round holes, a plurality of polygonal holes, or a combination of round and polygonal holes.

Various embodiments disclosed herein relate to a surgical saw blade having an upper surface and a lower surface. The saw blade may include a first end having right and left side edges, the first end being configured to connect to an oscillating head of a powered saw; a second end having a plurality of teeth thereon; and an elongated shank having right and left side edges, where the elongated shank connects the first and second ends. In various embodiments, a stopping surface configured to engage the oscillating head connects the first end to the elongated shank. In various embodiments, the stopping surface includes a first stopping surface connecting the right side edge of the first end of the saw blade to the right side edge of the elongated shank; and a second stopping surface connecting the left side edge of the first end to the left side edge of the elongated shank.

The surgical saw blade may further include at least three alignment holes on the elongated shank. The at least three alignment holes on the elongated shank may be freely distributed over the saw blade in a variety of ways. At least one alignment hole may be positioned near the first end of the saw blade, near a stopping surface. At least one alignment hole may be positioned near the second, cutting, end of the saw blade. A third alignment hole may be positioned near the first end of the saw blade, near the second end of the saw blade, or on the shank, between the first and second ends of the saw blade. At least two alignment holes may be positioned on one side of the saw blade, with a third hole being positioned on an opposite side of the saw blade.

In various embodiments, the surgical saw blade includes at least three alignment holes on the elongated shank, the alignment holes being distributed along the length or across the width of the saw blade. In various embodiments, the surgical saw blade includes at least two first alignment holes on the elongated shank, each alignment hole being in proximity to the second end of the surgical saw blade.

In various embodiments, the surgical saw blade includes at least two first alignment holes on the elongated shank, in proximity to the first and second stopping surfaces, and at least one second alignment hole on the elongated shank, in proximity to the second end of the surgical saw blade.

Various embodiments disclosed herein relate to a surgical saw blade with:
 a first end having right and left side edges, the first end being configured to connect to an oscillating head of a powered saw;
 a second end having a plurality of teeth thereon;
 an elongated shank connecting the first and second ends; and
 a stopping surface connecting the first end to the elongated shank. The stopping surface may be configured to engage the oscillating head so as to ensure correct positioning of the saw blade relative to the oscillating head.

In various embodiments, the second end of the saw blade may have planar upper and lower surfaces with a plurality of first teeth mounted thereon. The second end of the saw blade may have a constant thickness. Alternatively, the second end of the saw blade may have a variable thickness, with slots and/or grooves in the second end of the saw blade being configured to carry dust generated during a sawing operation away from the teeth on the saw blade.

In various embodiments, the second end of the saw blade may have a plurality of first teeth thereon, where each first tooth is mounted on a distal end of a tine. In various embodiments, each pair of adjacent tines is separated by a longitudinal slot extending from an upper surface of the saw blade to a lower surface of the saw blade, and a distal end of each longitudinal slot is bridged by a web connecting a corresponding pair of adjacent tines. In various embodiments, each longitudinal slot is configured to carry dust generated during a sawing operation away from the first teeth.

In various embodiments, a longitudinal groove or grooves extending partially through the thickness of the saw blade may be positioned between adjacent teeth, with the longitudinal groove or grooves being configured to carry dust generated during a sawing operation away from the teeth on the saw blade.

In various embodiments, the saw blade may further include at least two first alignment holes on the elongated shank, each first alignment hole being in proximity to a longitudinal slot. In various embodiments, each first alignment hole is in proximity to a different longitudinal slot. In various embodiments, the surgical saw blade may further include at least one second alignment hole on the elongated shank, in proximity to the stopping surface connecting the first end to the elongated shank of the saw blade.

Various embodiments disclosed herein relate to a surgical saw blade. The saw blade may include:
 a first end having an upper surface, a lower surface, and a hole extending from the upper surface to the lower surface, the first end being configured to connect to an oscillating head of a powered saw;
 a second end having a plurality of teeth thereon;
 an elongated shank connected to the second end; and
 a stopping surface connecting the first end and the elongated shank, the stopping surface being shaped so as to engage a mating surface of the oscillating head. In various embodiments, the stopping surface may be planar, so as to engage a flat mating surface on the oscillating head. In various embodiments, the stopping surface may be non-planar, e.g., curved, so as to engage a non-planar mating surface on the oscillating head.

In various embodiments, the upper surface and the lower surface of the first end may be configured to engage first and second clamping surfaces on the powered saw; and the hole in the first end is configured to engage an elevated ridge on at least one of the first and second clamping surfaces. The elongated shank may have an upper surface and a lower surface, with an elongated hole in the shank extending from the upper surface to the lower surface. The size of the elongated hole may be selected so as to optimize a dynamic stiffness of the saw blade, a resonant frequency of the saw blade, or both the dynamic stiffness and the resonant frequency of the saw blade. In various embodiments, the hole in the shank is configured to optimize the resonant frequency of the saw blade, so that the resonant frequency of the saw blade is greater than an oscillation frequency of the saw during a cutting operation. In various embodiments, the surgical saw blade may further include at least two alignment holes on the elongated shank, where a first alignment hole is in proximity to a second end of the saw blade and a second alignment hole is in proximity to the stopping surface.

Various embodiments disclosed herein relate to a surgical saw assembly, including:
 a. a surgical saw blade having an upper surface and a lower surface, with:
  a first end having right and left side edges;
  a second end having a plurality of teeth thereon;
  an elongated shank having right and left side edges, where the elongated shank connects the first and second ends; and
  a stopping surface connecting the first end to the elongated shank; and.
 b. a hand-held surgical saw handle, including:
  an oscillating head configured to vibrate the surgical saw blade laterally, including:
   a first surface configured to engage the right side edge of the first end of the surgical saw;
   a second surface configured to engage the left side edge of the first end of the surgical saw; and
   a third surface configured to engage the stopping surface; and
  at least two clamping surfaces configured to engage the first end of the saw blade;
   wherein a ridge may be positioned on at least one of the clamping surfaces, the ridge being configured to engage a hole extending through the first end of the saw blade.

In various embodiments, a surgical saw assembly includes:
 a. a surgical saw blade, with:
  a first end having an upper surface, a lower surface, and a hole extending from the upper surface to the lower surface, the first end being configured to connect to an oscillating head of a powered saw;
  a second end having a plurality of teeth thereon;
  an elongated shank connected to the second end; and
  a stopping surface connecting the first end and the elongated shank, the stopping surface being shaped so as to engage a surface of the oscillating head; and b. a hand-held surgical saw handle, including:
   an oscillating head configured to vibrate the surgical saw blade laterally, configured to engage the first end of the surgical saw blade and the stopping surface of the surgical saw blade;
   a first clamping surface configured to engage the upper surface of the first end of the saw blade;
   a second clamping surface configured to engage the lower surface of the first end of the saw blade; and
   an elevated ridge on at least one of the first and second clamping surfaces, the elevated ridge being configured to engage the hole in the first end of the saw blade.

BRIEF DESCRIPTION OF THE DRAWINGS

In order to better understand various exemplary embodiments, reference is made to the accompanying drawings, wherein.

DETAILED DESCRIPTION OF THE PREFERRED EMBODIMENTS OF THE INVENTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Figure 1:
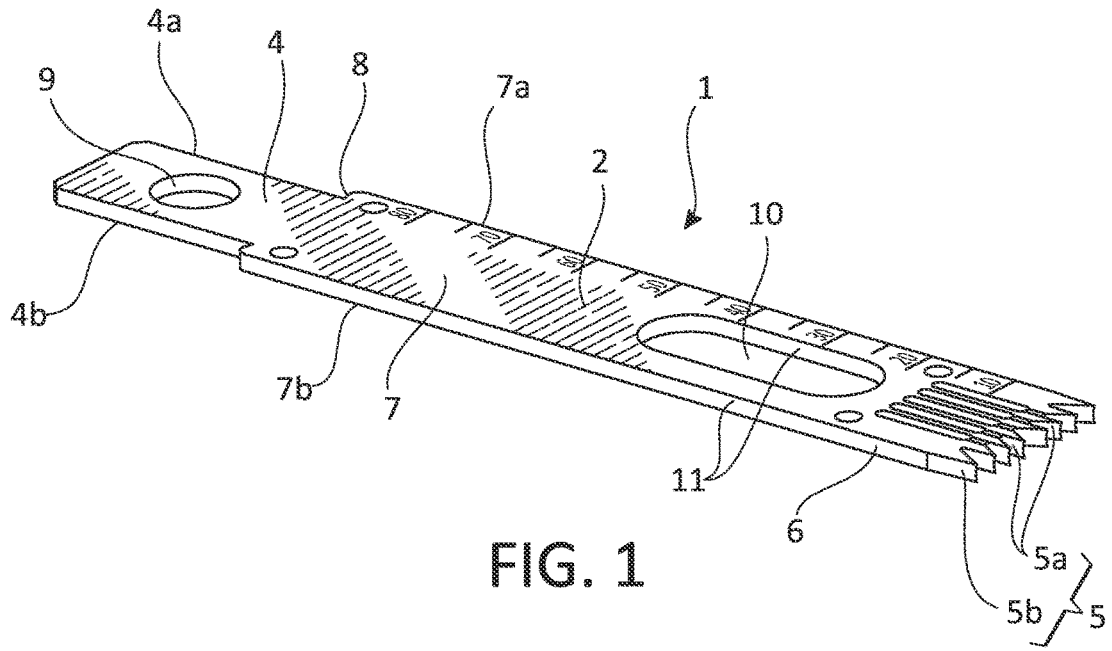
FIGS. 1 and 12 show a top perspective view of the surgical saw blade disclosed herein.

Referring now to the drawings, in which like numerals refer to like components or steps, there are disclosed broad aspects of various exemplary embodiments. FIG. 1 is a view of the surgical saw blade 1 having an upper surface 2 and a lower surface 3 (shown in FIG. 2). The saw blade may include a first end 4 having right side edge 4a and left side edge 4b, where the first end is configured to connect to an oscillating head of a powered saw. A second cutting end 6 of the saw blade has a plurality of teeth 5 thereon including inner teeth 5a and outer teeth 5b, where teeth 5b are at right and left side edges of the second end. An elongated shank 7 connects the first and second ends. Shank 7 may have right and left side edges 7a and 7b, respectively. In various embodiments, the first end 4 of saw blade 1 is narrower than the elongated shank 7, and a stopping surface 8 is at the connection of the first end to the elongated shank. The stopping surface 8 may be configured to engage the oscillating head of the powered saw so as to ensure correct positioning of the saw blade relative to the oscillating head.

In various embodiments, the elongated shank 7 has an upper surface and a lower surface, with an elongated hole 10 in the shank 7 extending from the upper surface of the shank to the lower surface. The elongated hole 10 may be configured to control a resonant frequency of the saw blade 1. The size of elongated hole 10 may also be selected so as to optimize a dynamic stiffness of the saw blade 1. The resonant frequency W is dependent on mass M and stiffness K by the equation:

$$W=\sqrt{K/M}$$

The resonant frequency can thus be increased by reducing mass, and/or increasing stiffness. As the presence of hole 10 reduces the overall mass of saw blade 1, it helps increase the resonant frequency of the saw blade. The shape of hole 10 may impact stiffness of the saw blade. The struts 11 in shank 7 connect the second end of the saw blade to the blade. The thickness of struts 11 is dependent on the width of hole 10. Changing the shape of hole 10 while holding the area of hole 10 constant, and thus holding the blade mass constant, impacts resonant frequency. If hole 10 is wide, the width of struts 11 may be small, reducing blade stiffness K and decreasing resonant frequency of the blade. Reducing the width of hole 10 without changing the area of hole 10, increases the width of struts 11, increasing the stiffness K of the blade 1, and consequently increasing the resonant frequency.

Also, changing the area of the hole 10 alters blade mass and impacts resonant frequency, with an increase in the area of hole 10 reducing mass M and increasing the resonant frequency. Resonant frequency may be optimized by balancing the area of hole 10, and the width of struts 11.

Various embodiments disclosed herein relate to a surgical saw blade having an upper surface and a lower surface with:
   a first end having right and left side edges, where the first end is configured to connect to an oscillating head of a powered saw which operates with a designed oscillation frequency;
   a second end having a plurality of teeth thereon; and
   an elongated shank connecting the first and second ends. In various embodiments, the elongated shank has an upper surface and a lower surface, with at least one hole in the shank extending from the upper surface to the lower surface, where the shape and size of the hole in the shank is configured to optimize the resonant frequency of the saw blade. The hole in the shank may be configured to ensure that a resonant frequency of the saw blade is greater than the oscillation frequency of the oscillating head of the powered saw, thereby ensuring that the saw blade does not resonate during use. In various embodiments, the hole may be a single elongated hole. In various embodiments, the hole in the shank may be an elliptical hole, a round hole, or a polygonal hole. In various embodiments, the hole in the shank may be a single large round hole. Some embodiments disclosed herein may include a series of multiple small holes in the shank, instead of a single round or elongated hole.

In various embodiments, the surgical saw blade has an elongated shank with an upper surface and a lower surface, with a plurality of holes in the shank extending from the upper surface to the lower surface. The plurality of holes may be configured to ensure that a resonant frequency of the saw blade is greater than an oscillation frequency of the oscillating head. The plurality of holes in the shank may be a plurality of round holes, a plurality of polygonal holes, or a combination of round and polygonal holes.

In various embodiments, the surgical saw blade 1 has a stopping surface 8 which includes a first stopping surface 8a connecting the right side edge 4a of the first end 4 of the saw blade to the right side edge 7a of the elongated shank 7 and a second stopping surface 8b connecting the left side edge 4b of the first end 4 to the left side edge 7b of the elongated shank 7. The first and second stopping surfaces may be configured to engage the oscillating head of the powered saw. In various embodiments shown in FIG. 1A, the second stopping surface 8b and the left side edge 4b may meet at an angle θ to form an angled surface on the left side of the saw blade, where θ may be an acute angle, a right angle, or an obtuse angle. Similarly, the first stopping surface 8a and the right side edge 4a may meet at a corresponding angle θ to form an angled surface on the right side of the saw blade. The right and left angled surfaces formed by the stopping surface 8 and the sides of the first end of the saw blade are configured to engage a corresponding angled surface on the oscillating head of the powered saw. When the right and left stopping surfaces 8a and 8b engage the oscillating head, the stopping surfaces prevent further longitudinal motion of the saw blade into the oscillating head, ensuring correct positioning of the saw blade. In various embodiments, the stopping surfaces 8a and 8b and may meet corresponding edges 4a and 4b at a defined angle θ, where stopping surfaces 8a and 8b may be planar surfaces or curved surfaces. Angle θ may be an acute angle, an obtuse angle, or a right angle. If the stopping surfaces 8a and 8b are planar surfaces, they are configured to engage corresponding planar surfaces on an oscillating head of a powered saw. If the stopping surfaces 8a and 8b are curved surfaces, they are configured to engage corresponding curved surfaces on an oscillating head of a powered saw. In various embodiments, intersections between the stopping surfaces 8a and 8b and the corresponding edges 4a and 4b may be rounded, where stopping surfaces 8a and 8b may be planar surfaces or curved surfaces. In embodiments where the intersections between the stopping surfaces and the corresponding edges 4a and 4b may be rounded, lines A which are tangent to the stopping surfaces 8a and 8b at a point adjacent to the intersection may meet edges 4a and 4b at the defined angle θ, as shown in FIG. 1A.

Figure 1A:
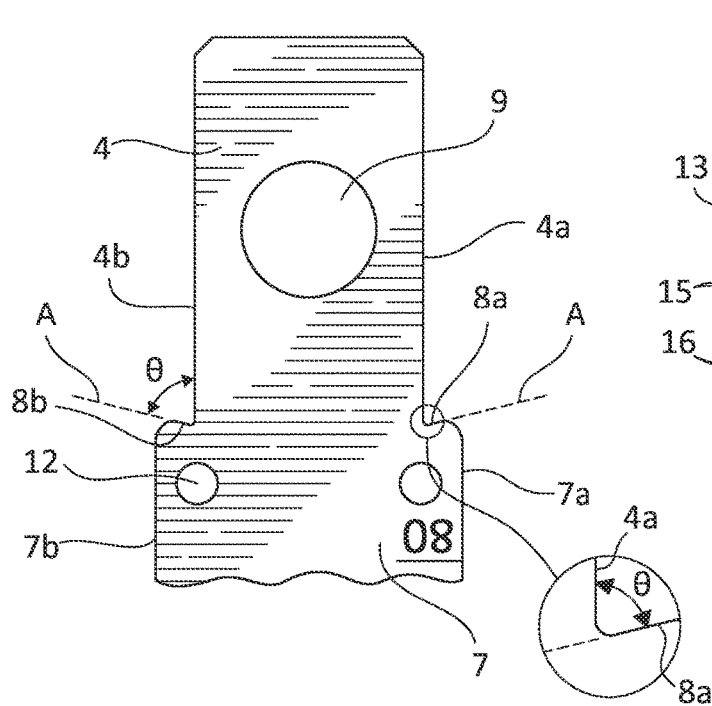
FIG. 1A shows a first end of the surgical saw blade of FIG. 1, configured for attachment to a powered saw.
Figure 2:
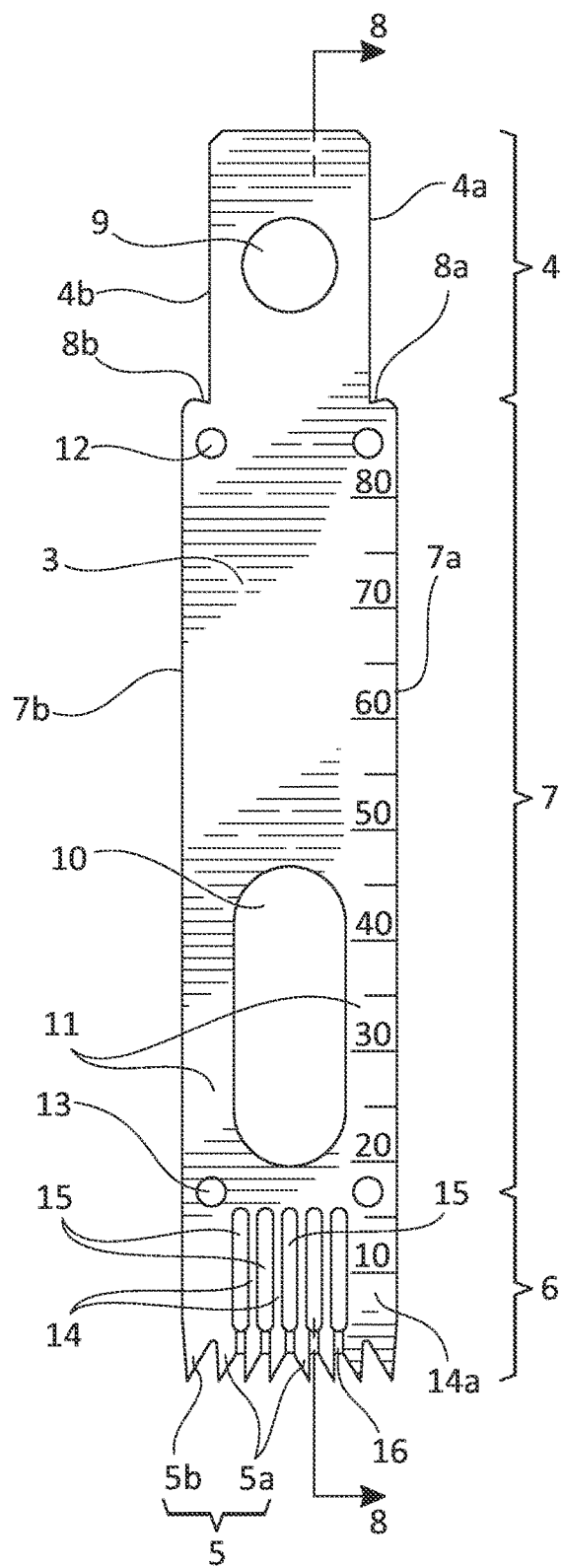
FIGS. 2 and 13 show a top plan view of the surgical saw blade of FIG. 1.

As shown in FIGS. 1A and 2, the first end 4 of the saw blade 1 may have an upper surface and a lower surface, with a hole 9 in the first end extending from the upper surface to the lower surface. The upper surface and the lower surface of the first end of the saw blade may be configured to engage first and second clamping surfaces on the powered saw, which will be further described later in this disclosure. The hole in the first end may be configured to engage an elevated ridge on at least one of the first and second clamping surfaces.

Various embodiments disclosed herein relate to a surgical saw blade having an upper surface and a lower surface. The saw blade may include a first end having right and left side edges, the first end being configured to connect to an oscillating head of a powered saw; a second end having a plurality of teeth thereon; and an elongated shank having right and left side edges, where the elongated shank connects the first and second ends. In various embodiments, at least one stopping surface configured to engage the oscillating head connects the first end to the elongated shank. In various embodiments, the stopping surface may include first and second stopping surfaces on opposing edges of the first end of the saw blade, where the first and second stopping surfaces together connect the first end of the saw blade to the elongated shank.

Figure 1B:
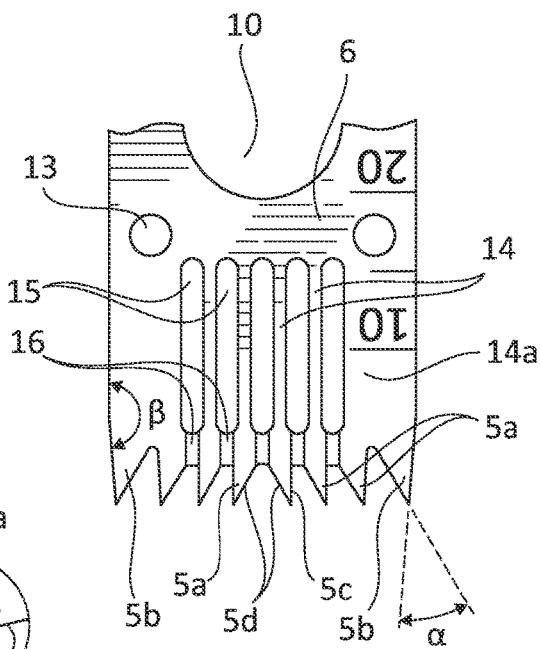
FIG. 1B shows a second cutting end of the surgical saw blade of FIG. 1.

The surgical saw blade may include at least three alignment holes on the elongated shank. The at least three alignment holes on the elongated shank may be freely distributed over the saw blade in a variety of ways. In various embodiments shown in FIG. 1A, at least one alignment hole 12 may be in proximity to at least one stopping surface 8a or 8b. At least one alignment hole 13 may be positioned near the second end 6 of the saw blade, in proximity to the cutting edge, as shown in FIG. 1B. At least one alignment hole may be positioned near the first end of the saw blade, near a stopping surface, and at least one alignment hole may be positioned near the second, cutting, end of the saw blade. A third alignment hole may be positioned near the first end of the saw blade, near the second end of the saw blade, or on the shank, between the first and second ends of the saw blade. At least two alignment holes may be positioned on one side of the saw blade, with a third hole being positioned on an opposite side of the saw blade. In various embodiments shown in FIG. 1A, an alignment hole 12 may be in proximity to each of stopping surfaces 8a and 8b.

In various embodiments, the surgical saw blade includes at least three alignment holes on the elongated shank, the alignment holes being distributed along the length or across the width of the saw blade. In various embodiments, the surgical saw blade includes at least two first alignment holes on the elongated shank, each alignment hole being in proximity to the second end of the surgical saw blade. In various embodiments, the surgical saw blade includes at least two first alignment holes on the elongated shank, in proximity to the first and second stopping surfaces, and at least one second alignment hole on the elongated shank, in proximity to the second end of the surgical saw blade.

FIG. 1B shows the cutting end 6 of the surgical saw blade. The cutting end 6 has a plurality of first teeth 5a mounted thereon. Each first tooth 5a is mounted on a distal end of a tine 14. Each pair of adjacent tines may be separated by a longitudinal slot 15, with a distal end of each longitudinal slot 15 being bridged by a web 16 connecting a corresponding pair of adjacent tines. When the saw blade is vibrated laterally by a powered saw, the surfaces of webs 16 are recessed from an upper and/or lower surface of the saw blade 1, thereby allowing sawdust and chips generated during a sawing operation to move around the webs 16 into longitudinal slots 16. The longitudinal slots 16 allow cut material generated at the tip of the cutting edge, at the teeth, to move away from the teeth 5a, preventing a buildup of cut material at the cutting edge during a sawing operation. In various embodiments shown in FIG. 1B, at least one alignment hole 13 may be in proximity to cutting end 6 of the surgical saw blade 1, e.g., near teeth 5 or longitudinal slots or grooves 15. In various embodiments shown in FIG. 1A, at least two alignment holes 13 may be in proximity to cutting end 6 of the surgical saw blade 1.

In various embodiments, the cutting end 6 of the surgical saw blade may have planar upper and lower surfaces with a plurality of first teeth mounted thereon. The second end of the saw blade may have a constant thickness, with no grooves 15 or other features therein. Alternatively, the second end of the saw blade may have a variable thickness, with slots 15 which extend through the full thickness of the cutting end 6. Alternatively, the second end of the saw blade may have teeth separated by a plurality of grooves, where each groove partially extends through the full thickness of the cutting end 6. Slots 15 and/or grooves in the second end of the saw blade are configured to carry dust generated during a sawing operation away from the teeth on the saw blade. In various embodiments, any pair of adjacent teeth on the second cutting end of the saw blade may be separated by a longitudinal groove or grooves.

Webs 16 may be thinner than the overall thickness of the saw blade, allowing cut material to travel over and/or under webs 16 into longitudinal slots 15 easily. The left and right edges of the cutting end 6 may have tines 14a. Tines 14a may have a single tooth, and be structurally similar to tines 14, except that they have an adjacent tine on only one inner side. Alternatively, tines 14a may be of increased thickness, relative to the other tines 14, and may each have two teeth at the distal end. In various embodiments, there may be an outer tooth 5b and an inner tooth 5a on each tine 14a, where each tooth 5a may be positioned at the end of tine 14a at the entrance to a longitudinal slot 15. The tooth 5a at the end of tine 14a may be connected with a tooth 5a on an adjacent tine 14 by a web 16. An outer tooth on each tine 14a is a tooth 5b, where tooth 5b is adjacent to a tooth 5a on tine 14a. In various embodiments, the tooth 5a at the end of tine 14a and the tooth 5b may or may not be separated by a longitudinal slot or groove, such as groove 14. In various embodiments, outer tines 14a and the inner tines 14 each have a similar width, with a single tooth. In various embodiments, outer tines 14a have two teeth, and may be from two to six times wider, or about four times wider, than the inner tines 14. The increased thickness of tines 14a may increase the stiffness of the cutting end 6 of saw blade 1. As seen in FIG. 1B, the teeth 5 may be asymmetric, where each tooth 5a and 5b may have an outer cutting edge 5c and an inner cutting edge 5d, where edges 5c and 5d meet at an acute angle, where the outer cutting surfaces 5c are nearer to an edge of the saw blade 1 than the inner cutting edges 5d. In various embodiments, the outer edge 5c of each tooth 5a and 5b may be parallel or nearly parallel to an edge of the saw blade 1, forming an angle β, where is β between 160° and 180°, with the edge of the saw blade. In various embodiments, the inner edge 5d of each tooth 5a and 5b may form an angle α of between 30° and 45° with a corresponding outer edge 5c. In various embodiments, the teeth 5 may each be asymmetric about a line parallel to an edge of saw blade 1. In various embodiments, the saw blade 1 may include a combination of symmetric and asymmetric teeth.

Figure 3:
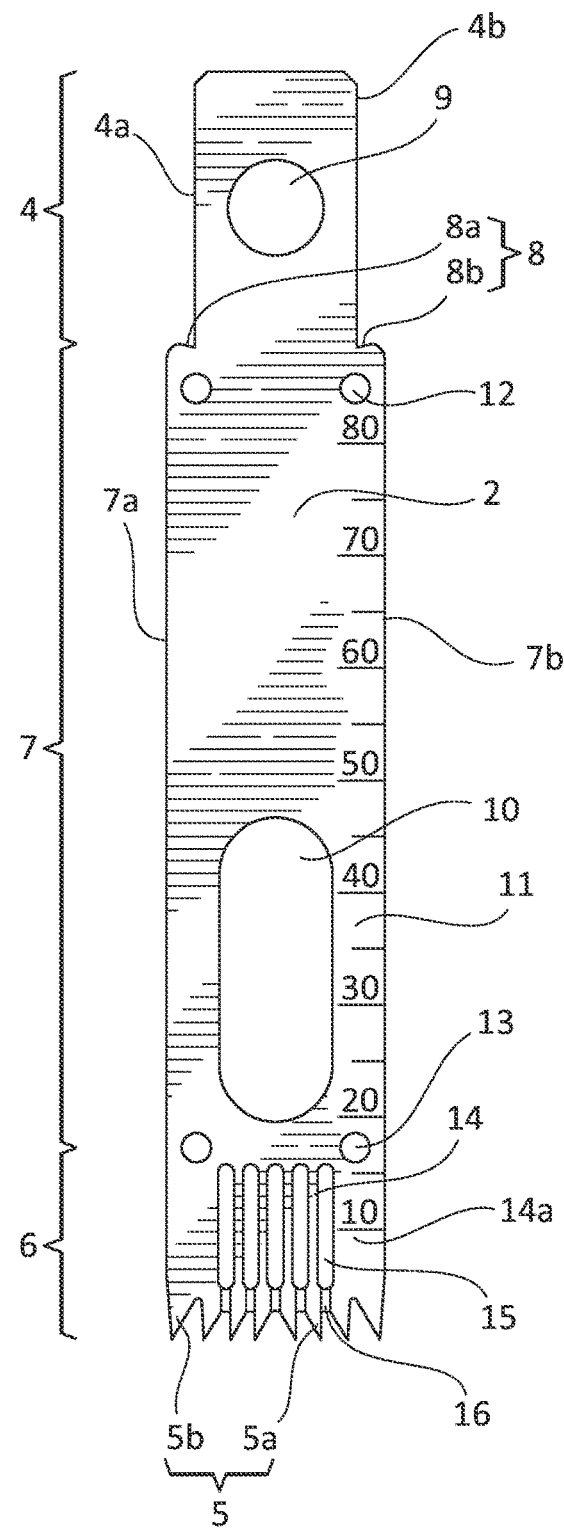
FIGS. 3 and 14 show a bottom plan view of the surgical saw blade of FIG. 1.

FIGS. 2 and 3 show top and bottom plan views of the surgical saw blade of FIG. 1, respectively. The relationship of the stopping surfaces 8a and 8b to the edges of the shank 7 and the first end 4, configured for attachment to a powered saw, is seen in FIGS. 2 and 3. Elongated shank 7 generally extends from stopping surfaces 8a and 8b to alignment holes 13. The cutting end of the saw blade may be considered to extend from alignment holes 13 to the tips of teeth 5a and 5b.

Figure 4:
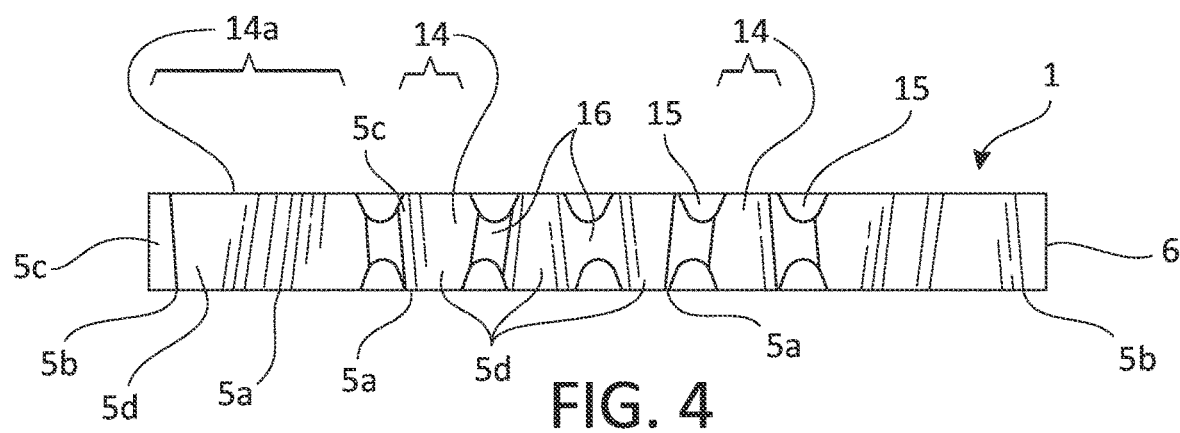
FIG. 4 shows a front elevation view of the surgical saw blade of FIG. 1, showing the cutting end.

FIG. 4 shows an elevation view of the cutting end 6 of the surgical saw blade 1. At the outer edges of the cutting end 6 are two asymmetric teeth 5b. Each asymmetric tooth 5b may include an outer cutting edge 5c, which is parallel or nearly parallel to an edge of saw blade 1, and an inner cutting edge 5d. Inner cutting edge 5d may form an acute angle with a line which is parallel to the edge of saw blade 1. Inner teeth 5a may also be asymmetric, with an outer cutting edge 5c which is nearly parallel to an edge of saw blade 1, and an inner cutting edge 5d which forms an acute angle with the edge of saw blade 1. The saw blade 1 may have a plane of symmetry along a longitudinal axis, so that teeth 5 on a left side of cutting end 6 may be mirror images of corresponding teeth on the right side. If there is such a plane of symmetry, each tooth 5a and each tooth 5b has the same width at an upper surface of cutting end 6 and the same width at a lower surface of cutting end 6, where the widths at the upper and lower surfaces of the cutting edge may be the same or different. Alternatively, the cutting end 6 may have two-fold rotational symmetry when rotated 180° about a longitudinal axis of the saw blade 1.

If the cutting end has two-fold rotational symmetry, all teeth may have a constant width from the upper surface of cutting edge 6 to the lower surface of cutting edge 6. Alternatively, if two-fold rotational symmetry is present, the width of each tooth 5 on a right side of saw blade 6 may change from a first selected width at an upper surface of cutting end 6 to a second selected width at a lower surface of cutting end 6. To maintain rotational symmetry, the width of each tooth 5 on a left side of saw blade 6 may change from the second selected width at an upper surface of cutting end 6 to the first selected width at a lower surface of cutting end 6. FIG. 4 shows a cutting end 6 with rotational symmetry, where teeth 5a on cutting end 6 are:

narrower at an upper surface than a lower surface on the right side of cutting end 6; and narrower at a lower surface than an upper surface on the left side of cutting end 6.

If a plane of symmetry or rotational symmetry is present about saw blade 1, the inner cutting edges 5d of corresponding teeth on opposite sides of cutting end 6 face each other. Between any two adjacent teeth 5a, there is a longitudinal slot 15, with an opening visible in FIG. 4. The openings to the longitudinal slots 15 are visible in FIG. 4, with the opening to each slot 15 being partially obstructed by a web 16. Each web 16 links two tines carrying adjacent teeth 15a, and prevents relative movement between adjacent teeth 15a by holding the tines a fixed distance apart.

Figure 5:
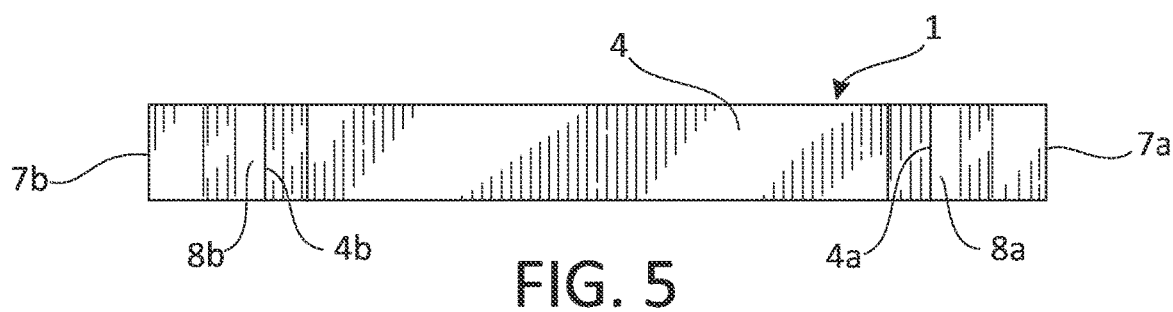
FIGS. 5 and 15 show a rear elevation view of the surgical saw blade of FIG. 1.

FIG. 5 shows an elevation view of the first end 4 of the surgical saw blade 1, where end 4 is configured for attachment to a powered saw. As seen in FIG. 5, stopping surface 8a connects the right side edge 4a of the first end 4 of the saw blade to the right side edge 7a of the elongated shank 7; and stopping surface 8b connects the left side edge 4b of the first end 4 to the left side edge 7b of the elongated shank 7.

Figure 6:
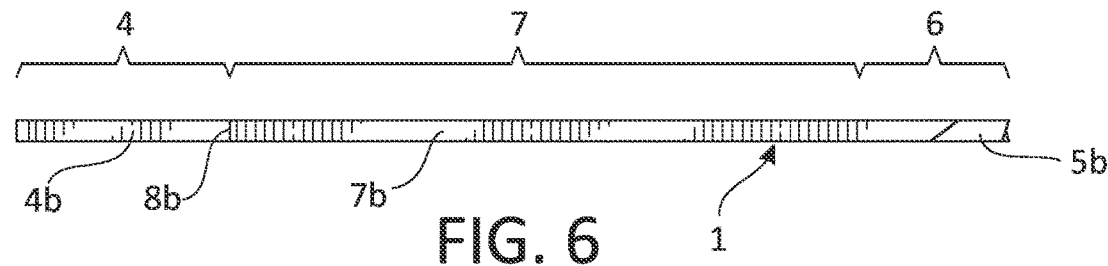
FIGS. 6 and 16 show a right elevation view of the surgical saw blade of FIG. 1.
Figure 7:
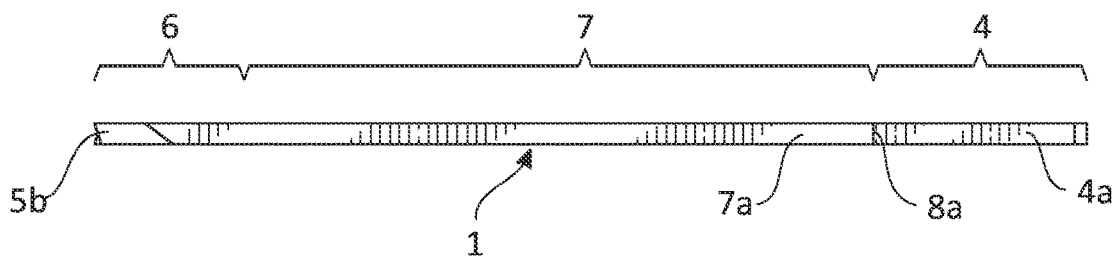
FIGS. 7 and 17 shows a left elevation view of the surgical saw blade of FIG. 1.

FIGS. 5 and 6 show right and left elevation views of the surgical saw blade 1.

Figure 8:
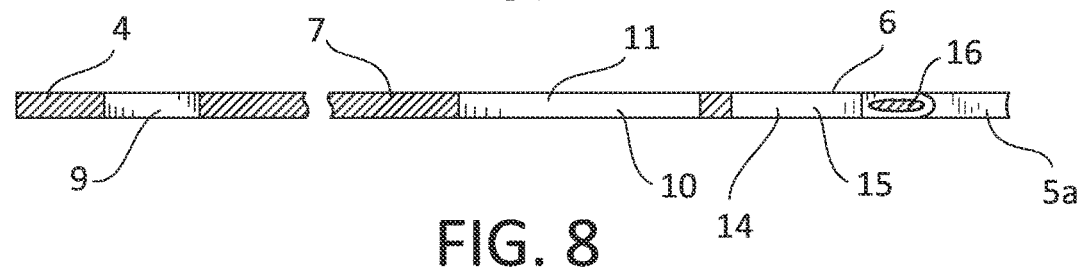
FIG. 8 shows a three-dimensional cross section view of the surgical saw blade of FIG. 1, taken in the direction of arrows 8 in FIG. 2, so that features in the plane of the cross section or behind the plane of the cross section are visible.

FIG. 8 shows a three-dimensional cross section view of the saw blade 1 of FIG. 1, seen from the perspective of arrows 8 in FIG. 2. The surgical saw blade 1 has a first end 4 configured to connect to an oscillating head of a powered saw, second cutting end 6 with a plurality of teeth thereon, including inner tooth 5a shown in FIG. 8, and an elongated shank 7 connecting the first end 4 and the cutting end 6. As seen in FIG. 8, the first end 4 of the saw blade 1 may have a hole 9 in the first end extending from an upper surface of the saw blade to a lower surface. In various embodiments, the elongated shank 7 has at least one hole 10 in the shank 7, extending from an upper surface of the shank to a lower surface. The hole 10 may be configured to control a resonant frequency of the saw blade 1. In various embodiments, the shape and size of hole 10 is configured to ensure that a resonant frequency of the saw blade 1 is higher than an oscillation frequency of the saw blade during a sawing operation. In various embodiments, saw blade 1 is configured to be attached to an oscillating surgical saw head, with hole 10 being configured to ensure that a resonant frequency of the saw blade 1 is higher than an oscillation frequency of the saw head. When viewing the cross section view of FIG. 9, hole 10 may be viewed in the foreground, with a rear edge of elongated hole 10 defining an inner edge of a strut 11. Strut 11 in shank 7 is visible at the rear surface of elongated hole 10. Each tooth 5a is adjacent to the opening of at least one longitudinal slot 15, with adjacent longitudinal slots 15 being connected by web 16.

In various embodiments, the hole 10 in the shank may be a single elongated hole, a single elliptical hole, or a single large round hole. Some embodiments disclosed herein may include a series of multiple small holes 10 in the shank, instead of a single round, elliptical, or elongated hole. In some embodiments including a series of multiple small holes 10 in the shank, the small holes 10 may each have the same geometry, e.g., the series of small holes may be a series of round holes, a series of elliptical holes, or a series of polygonal holes. In some embodiments including a series of multiple small holes in the shank, the small holes 10 may have different geometries, e.g., a series of round holes in combination with polygonal holes or a series of square holes in combination with rectangular or parallelogram-shaped holes.

Figure 9:
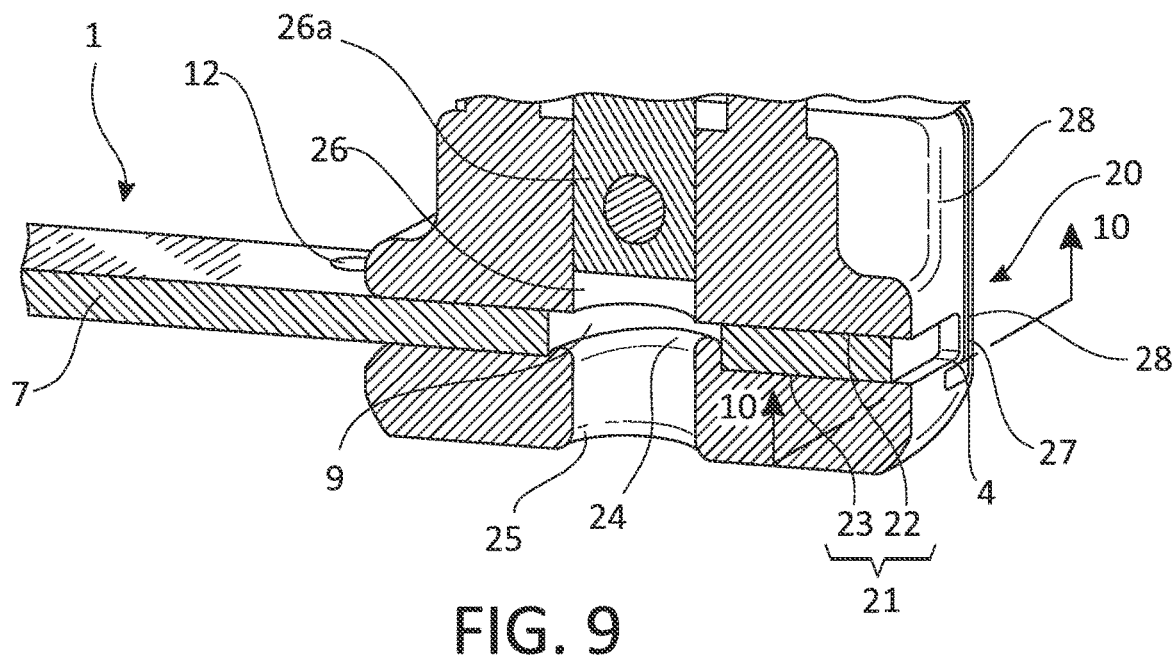
FIGS. 9 and 10 show two views of the saw blade of FIG. 1 connected to an oscillating head of a powered saw.

FIG. 9 shows the first end 4 of the saw blade 1 being mounted in a hand-held surgical saw handle 20 of a powered saw. The powered saw handle 20 includes two clamping surfaces 21, and may include upper and lower clamping surfaces 22 and 23, respectively. The upper clamping surface 22 may be a lower surface of an oscillating head 28 of the powered saw handle 20. The lower clamping surface 23 may be mounted on a clamping sleeve 27, where the clamping sleeve 27 may be raised or lowered independently of the oscillating head 28. In the configuration of FIG. 9, the clamping sleeve 27 may be lowered relative to clamping surface 22, so as to increase the gap between clamping surfaces 22 and 23 and allow the first end 4 of the saw blade 1 to be inserted therebetween. The first end 4 of the saw blade 1 may then be clamped between clamping surfaces 22 and 23 by raising the clamping sleeve 27 relative to clamping surface 22.

In various embodiments, a first hole 26 extends through oscillating head 28 and the upper clamping surface 22. A corresponding hole 25 extends into the lower clamping surface 23, so that holes 25 and 26 are aligned with each other. When saw blade 1 is properly inserted into the oscillating saw, between the clamping surfaces 21, hole 9 in the saw blade is aligned with each of holes 25 and 26 in the powered saw handle 20. A peg 26a may be mounted in hole 26 in the oscillating head 28, and may be passed through hole 9 in the saw blade and into hole 25 in the clamping sleeve 27, in the direction of arrow A. Thus, peg 26a secures the saw blade 1 in the powered saw handle 20, so as to prevent saw blade 1 from disengaging from the saw handle 20.

In various embodiments, the first hole 26 extending through oscillating head 28 and the corresponding hole 25 extending into the lower clamping surface 23 may each have a common radius $r_1$, which is about equal to the radius of peg 27. In various embodiments, the hole 9 in saw blade 1 may have a radius $r_2$, which is greater than $r_1$. In various embodiments, at least one of the upper and lower clamping surfaces 22 and 23 has a ridge 24 thereon, where ridge 24 has an outer diameter of $r_2$ and a width of w, where $w=r_2-r_1$. Thus, the ridge has an outer edge which is configured to engage hole 9 on saw blade 1. the ridge has an outer edge which is configured to engage peg 26a. The ridge 24 prevents movement of the saw blade 1 relative to the clamping surfaces 21 when the oscillating head 28 vibrates saw blade 1.

Figure 10:
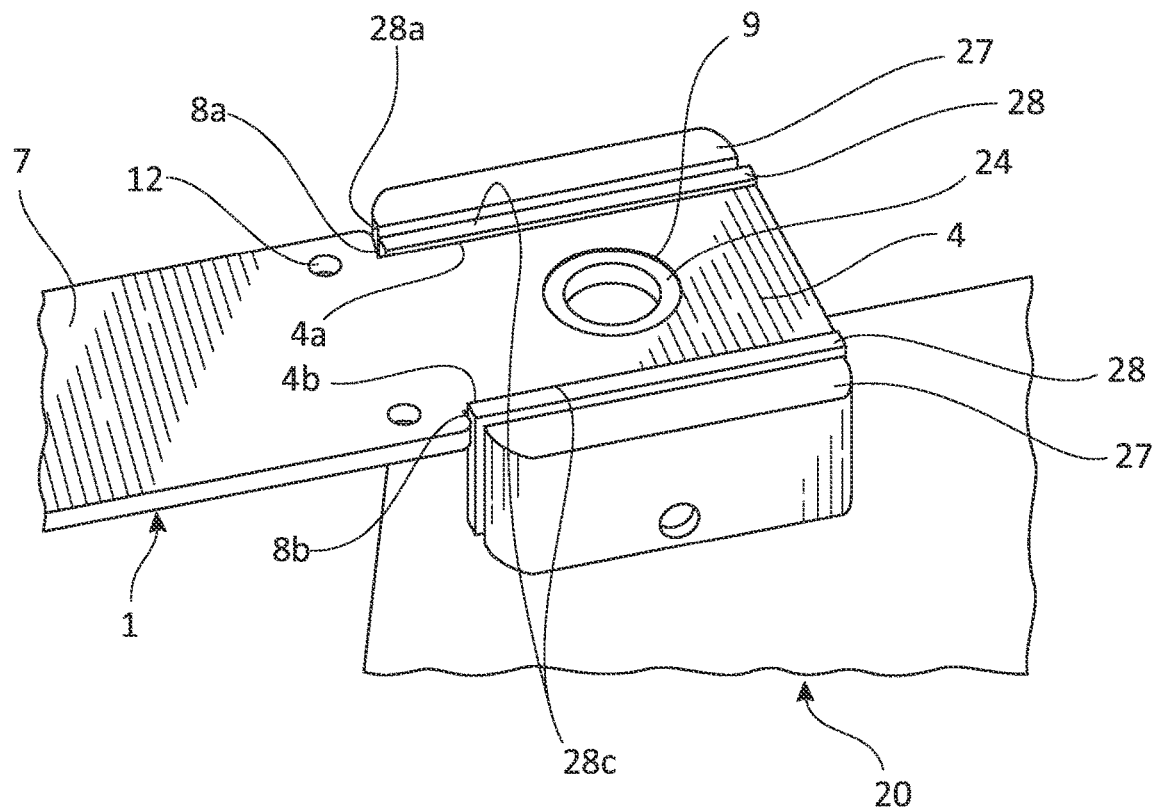

FIG. 10 is a view of the saw blade 1 mounted in powered saw handle 20, seen in the direction of arrows 10 in FIG. 9, along the plane of the lower clamping surface 23. The first end 4 is positioned so that edges 4a and 4b of the first end contact opposed contact surfaces 28c of the oscillating head 28. The oscillating head 28 is configured to vibrate the saw blade laterally, from right to left, through movement of the planar contact surfaces 28c. The oscillating head does not have a pivoting connection to the blade, so that lateral movement of the saw blade at shank 7 near vibrating head 28 is similar in amplitude to lateral movement of the cutting end 6 (not shown in FIG. 10) of saw blade 1.

A first stopping surface 28a on oscillating head 28 contacts the stopping surface 8a on saw blade 1. A second stopping surface 28b on oscillating head 28 contacts the stopping surface 8b on saw blade 1. In various embodiments, stopping surface 28a and 28b of the oscillating head 28, which may be curved or planar, each are configured to mate with a corresponding stopping surface 8a or 8b. Stopping surfaces 8a and 8b on the saw blade 1 may each make direct surface-to-surface contact with a stopping surface 28a or 28b on the oscillating head 28. As discussed above, the ridge 24 fits within hole 9 on the saw blade 1.

Figure 11:
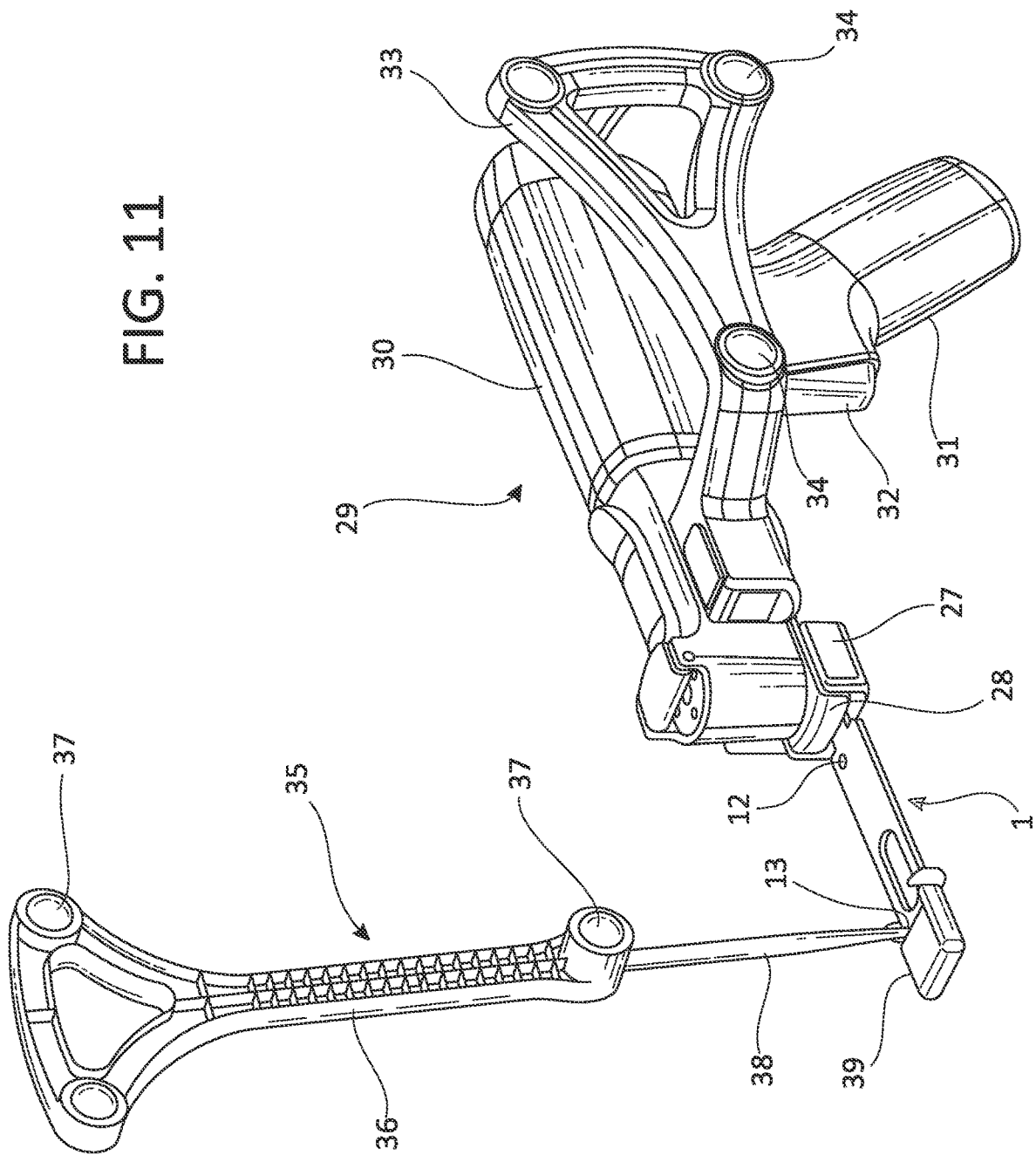
FIG. 11 shows an alignment tool used to ensure proper alignment of the saw blade of FIG. 1.
Figure 12:
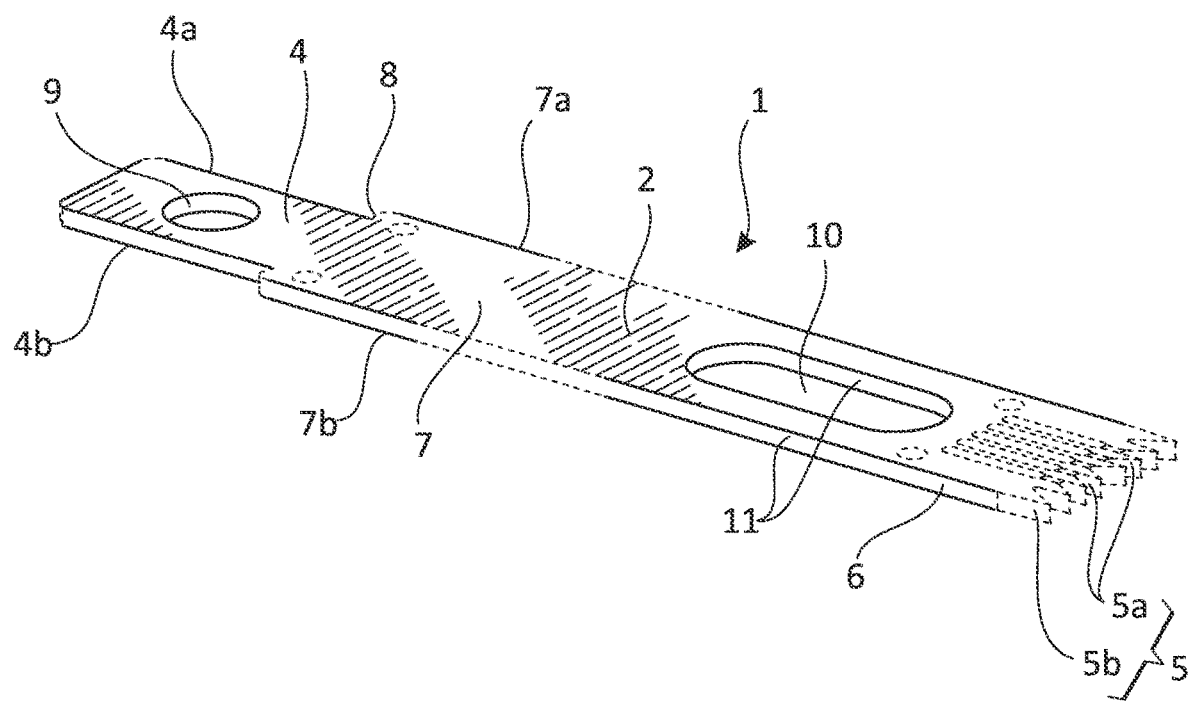
Figure 13:
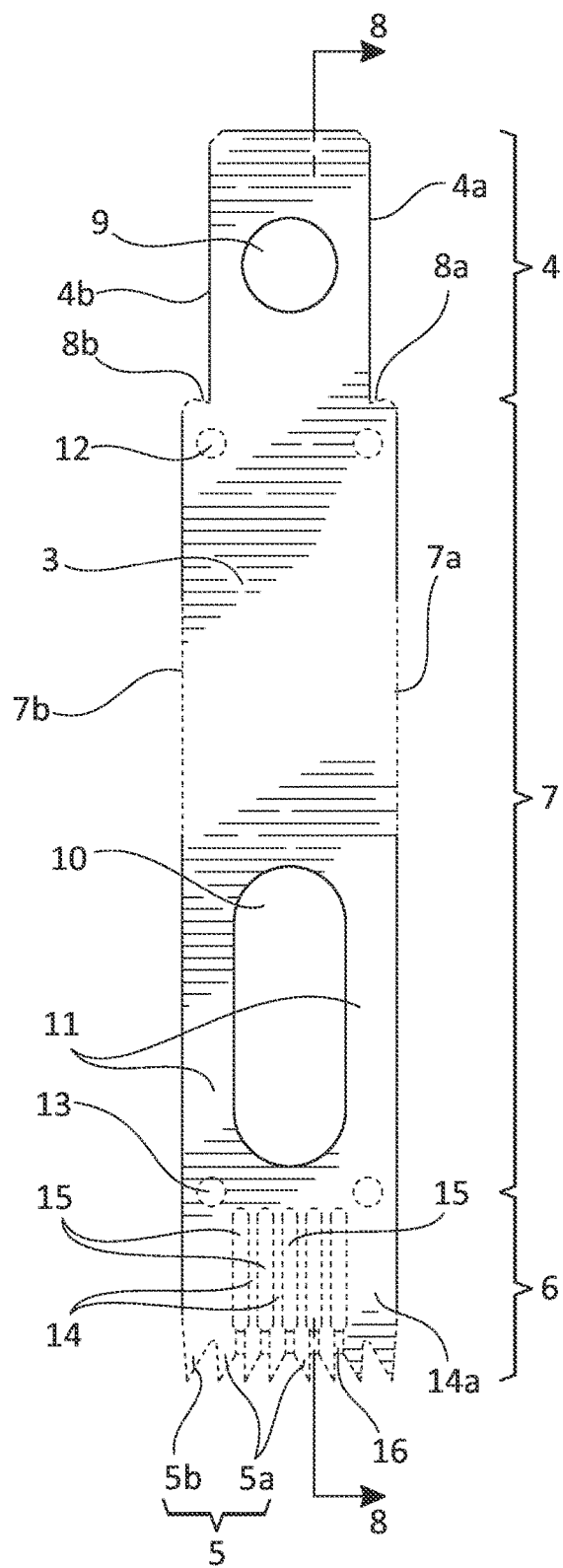
Figure 14:
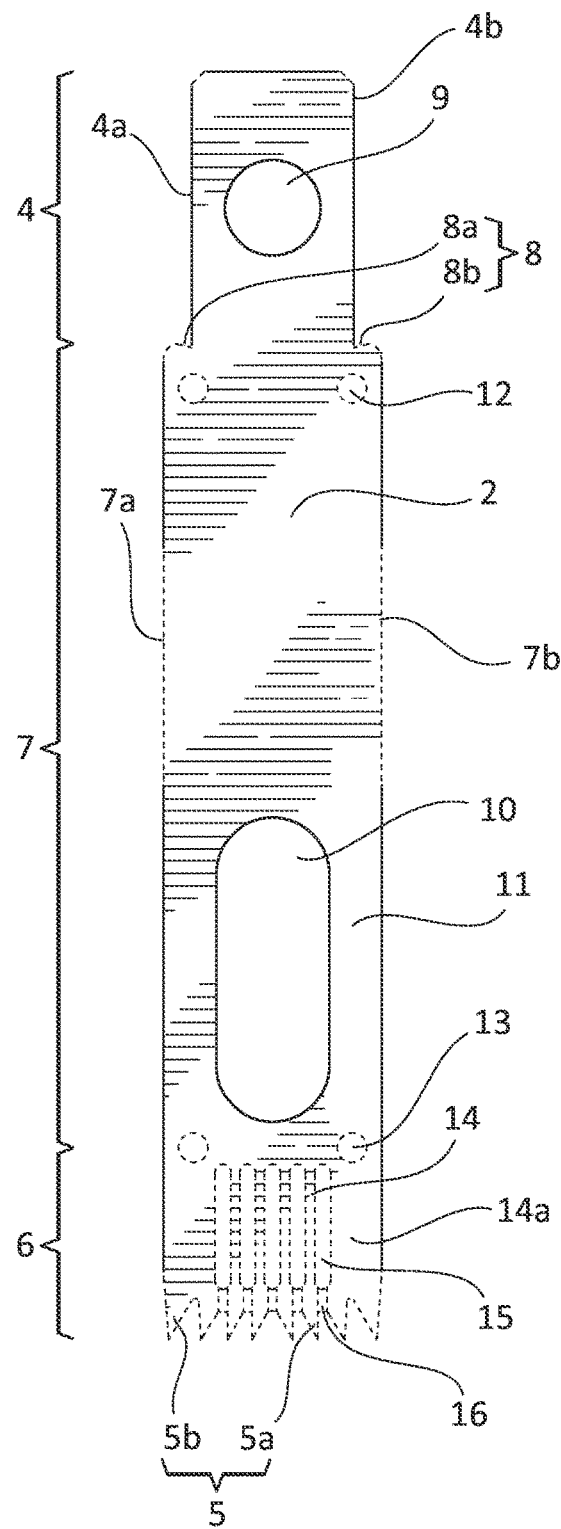
Figure 15:
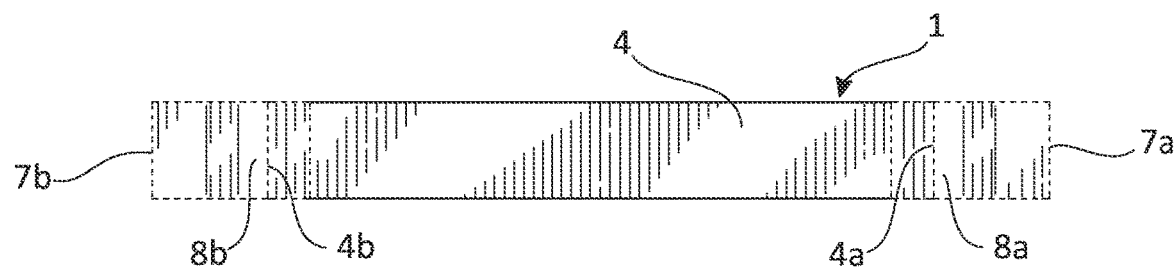
Figure 16:
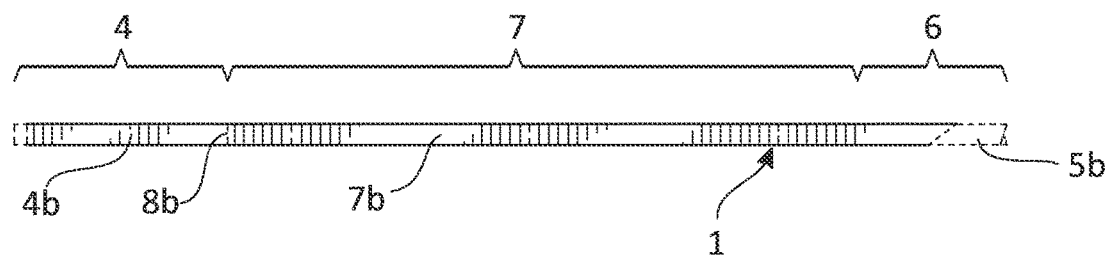
Figure 17:
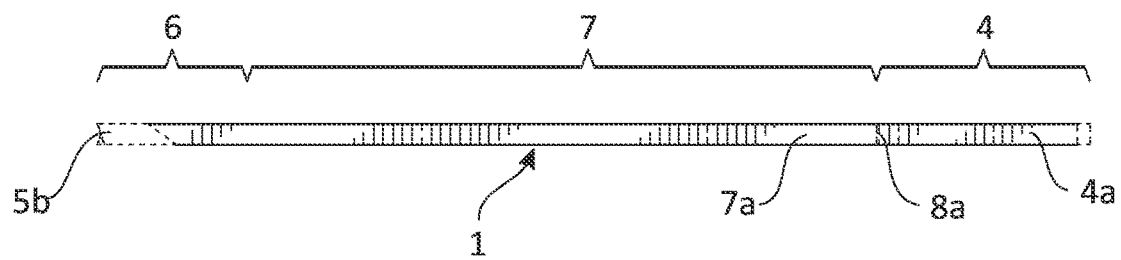

FIG. 11 shows saw blade 1 in combination with a surgical saw 29, where surgical saw 20 includes a barrel 30, a handle 31, a trigger 32, and an oscillating head 28. Saw blade 1 is connected to surgical saw 29 via clamping sleeve 27. A cover 39 is mounted over the cutting end of saw blade 1. A saw array 33 with a plurality of markers 34 is mounted to surgical saw 29. A positioning marker 35 is also shown in FIG. 11, where the positioning marker 35 includes a positioning array 36 with a plurality of markers 37 and a pointer 38 with a sterile pointer tip. The sterile pointer tip on pointer 38 fits into one of alignment holes 12 and 13 on saw blade 1. Markers 34 and 37 are then imaged with a camera, and used to determine the precise position of positioning array 36 relative to saw array 33. Since the length of the pointer 38 is known, this allows a determination of the position of saw blade 1 relative to saw array 33, allowing a user to determine a position of saw blade 1 relative to the surgical saw 29. In various embodiments, the sterile pointer tip on pointer 38 may be individually positioned in two or three of the alignment holes 12 and 13 on saw blade 1. For each alignment hole 12 and 13, markers 34 and 37 may be used to determine the precise position of positioning array 36 relative to saw array 33 at each alignment hole. allowing a determination of the position of saw blade 1 relative to saw array 33 at multiple points, so that a user may determine a cutting plane of saw blade 1.

Although the various embodiments have been described with reference to certain aspects thereof, it should be understood that the disclosed subject matter is capable of other embodiments and its details are capable of modifications in various respects. As is readily apparent to those skilled in the art, variations and modifications can be affected while remaining within the spirit and scope of the disclosure. Accordingly, the foregoing disclosure, description, and figures are for illustrative purposes only and do not in any way limit the invention, which is defined only by the claims.

What is claimed is:

1. A surgical saw blade configured to connect to an oscillating head of a powered saw, the oscillating head having two blade-engaging surfaces and a first angled stopping surface;
the saw blade comprising:
an upper surface and a lower surface;
a proximal end having right and left side edges, the right and the left side edges of the proximal end being configured to engage the blade-engaging surfaces of the oscillating head;
a distal end having a plurality of teeth thereon;
an elongated shank connecting the proximal end to the distal end;
wherein the proximal end is narrower than the shank, and a second angled stopping surface connects the proximal end to the elongated shank;
the second angled stopping surface being configured to make surface-to-surface contact with the first angled stopping surface so as to ensure correct longitudinal positioning of the saw blade relative to the oscillating head,
wherein the second angled stopping surface forms an acute angle $\theta$ with at least one of the right and the left side edges of the proximal end.

2. The surgical saw blade of claim 1, wherein the second angled stopping surface comprises:
a right stopping surface connecting the right side edge of the proximal end to a right side edge of the elongated shank;
a left stopping surface connecting the left side edge of the proximal end to a left side edge of the elongated shank; and
wherein the right and the left stopping surfaces are each configured to engage the oscillating head.

3. The surgical saw blade of claim 1, further comprising at least two alignment holes on the elongated shank, each alignment hole being:
in proximity to the distal end of the surgical saw blade; or
distributed along a length or across a width of the surgical saw blade.

4. A surgical saw assembly, comprising, in combination:
the surgical saw blade of claim 1; and
a hand-held surgical saw handle, comprising:
the oscillating head having the two blade-engaging surfaces and the first angled stopping surface, the oscillating head being configured to vibrate the surgical saw blade laterally, wherein:
the two blade-engaging surfaces are configured to engage the right side edge and the left side edge of the proximal end of the surgical saw blade;
the first angled stopping surface is configured to engage the second angled stopping surface; and
the oscillating head further comprises at least two clamping surfaces configured to engage the proximal end of the surgical saw blade;
wherein at least one of the at least two clamping surfaces includes a ridge, the ridge being configured to engage a hole extending through the proximal end of the surgical saw blade.

5. A surgical saw assembly configured to determine a cutting plane, comprising, in combination:
the surgical saw blade of claim 3;
a positioning device comprising a first positioning marker and a pointer with a pointer tip, the pointer tip being configured to engage one of the alignment holes;
an imaging system; and
a hand-held surgical saw handle with a second positioning marker, comprising:
the oscillating head having the two blade-engaging surfaces and the first angled stopping surface, the oscillating head being configured to vibrate the surgical saw blade laterally, wherein:
the two blade-engaging surfaces are configured to engage the right side edge and the left side edge of the proximal end of the surgical saw blade;
the first angled stopping surface is configured to engage the second angled stopping surface; and
the oscillating head further comprises at least two clamping surfaces configured to engage the proximal end of the surgical saw blade;
wherein at least one of the at least two clamping surfaces includes a ridge, the ridge being configured to engage a hole extending through the proximal end of the surgical saw blade;
wherein the imaging system is configured to determine the position of the first positioning marker relative to the second positioning marker.

6. A surgical saw blade having an upper surface and a lower surface, the saw blade comprising:
a proximal end having a peripheral edge, the proximal end being configured to connect to an oscillating head of a powered saw;
a distal end having a plurality of tines thereon, each tine having a tooth thereon, each pair of adjacent tines being separated by a longitudinal slot extending from the upper surface to the lower surface;
an elongated shank having right and left side edges, where the elongated shank connects the proximal and distal ends;
wherein the proximal end is narrower than the shank, and a stopping surface connects the proximal end to the elongated shank;
the stopping surface being configured to engage the oscillating head so as to ensure correct positioning of the saw blade relative to the oscillating head;
wherein:
the proximal end has a hole extending therethrough, the hole having a continuous edge, wherein the continuous edge of the hole is isolated from the peripheral edge of the proximal end;
the proximal end is configured to engage first and second clamping surfaces on the powered saw; and
the hole in the proximal end is configured to engage an elevated ridge on at least one of the first and second clamping surfaces.

7. The surgical saw blade of claim 6, further comprising at least two alignment holes on the elongated shank.

8. A surgical saw assembly, comprising, in combination:
the surgical saw blade of claim 6; and
a hand-held surgical saw handle, comprising:
an oscillating head configured to vibrate the surgical saw blade laterally, the oscillating head being configured to engage the proximal end of the surgical saw blade and the stopping surface of the surgical saw blade;

a first clamping surface configured to engage an upper surface of the proximal end of the surgical saw blade;

a second clamping surface configured to engage a lower surface of the proximal end of the surgical saw blade; and an elevated ridge on at least one of the first and second clamping surfaces, the elevated ridge being configured to engage the hole in the proximal end of the surgical saw blade.

9. A surgical saw assembly configured to determine a cutting plane, comprising, in combination:

the surgical saw blade of claim 7;

a positioning device comprising a first positioning marker and a pointer with a pointer tip, the pointer tip being configured to engage one of the alignment holes;

an imaging system; and a hand-held surgical saw handle with a second positioning marker, comprising:

an oscillating head configured to vibrate the surgical saw blade laterally, the oscillating head being configured to engage the proximal end of the surgical saw blade and the stopping surface of the surgical saw blade;

a first clamping surface configured to engage an upper surface of the proximal end of the surgical saw blade;

a second clamping surface configured to engage a lower surface of the proximal end of the surgical saw blade; and an elevated ridge on at least one of the first and second clamping surfaces, the elevated ridge being configured to engage the hole in the proximal end of the surgical saw blade;

wherein the imaging system is configured to determine the position of the first positioning marker relative to the second positioning marker.

10. The surgical saw blade of claim 6, wherein:

each longitudinal slot has a proximal end and a distal end; and the distal end of each longitudinal slot is bridged by a web connecting a corresponding pair of adjacent tines.

* * * * *